(12) United States Patent
Reddy et al.

(10) Patent No.: US 6,933,389 B2
(45) Date of Patent: Aug. 23, 2005

(54) PROCESS FOR PREPARATION OF CRYSTALLINE FORM-1 OF PANTOPRAZOLE SODIUM SESQUIHYDRATE

(75) Inventors: Manne Satyanarayana Reddy, Hyderabad (IN); Sajja Eswaraiah, Hyderabad (IN); Vijayavitthal Thippannachar Mathad, Hyderabad (IN); Pondichetty Anilkumar, Hyderabad (IN); Elati Ravi Ram Chandrashekar, Hyderabad (IN); Govindan Shanmugam, Hyderabad (IN)

(73) Assignees: Dr. Reddy's Laboratories Limited, Hyderabad (IN); Dr. Reddy's Laboratories, Inc., Upper Saddle River, NJ (US)

( * ) Notice: Subject to any disclaimer, the term of this patent is extended or adjusted under 35 U.S.C. 154(b) by 31 days.

(21) Appl. No.: 10/653,694

(22) Filed: Sep. 2, 2003

(65) Prior Publication Data

US 2004/0186139 A1 Sep. 23, 2004

(30) Foreign Application Priority Data

Sep. 2, 2002 (IN) .................................. 648/MAS/2002

(51) Int. Cl.$^7$ ............................................ C07D 401/12
(52) U.S. Cl. ...................................................... 546/273.7
(58) Field of Search ...................................... 546/273.7

(56) References Cited

U.S. PATENT DOCUMENTS

2004/0177804 A1 * 9/2004 Finkelstein et al.
2004/0235904 A1 * 11/2004 Finkelstein et al.

* cited by examiner

*Primary Examiner*—Patricia L. Morris
(74) *Attorney, Agent, or Firm*—Edward D. Pergament; Robert A. Franks

(57) ABSTRACT

An improved process for making crystalline Form-I of Pantoprazole sodium sesquihydrate is provided.

10 Claims, 2 Drawing Sheets

PROCESS FOR PREPARATION OF CRYSTALLINE FORM-1 OF PANTOPRAZOLE SODIUM SESQUIHYDRATE

CROSS-REFERENCE TO RELATED APPLICATION

This application claims priority of Indian Patent Application No. 648/MAS/2002, filed Sep. 2, 2002, the disclosure of which is incorporated herein by reference in its entirety.

BACKGROUND OF THE INVENTION

The drug pantoprazole sodium sesquihydrate (5-(Difluoromethoxy)-2-[[(3,4-dimethoxy-2-pyridinyl)methyl]sulfinyl]-1H-benzimidazole sodium sesquihydrate) is used in the treatment of gastroesophageal reflux disease (GERD), reflux esophagitis, gastric ulcers, duodenal ulcers and Zollinger-Ellison Syndrome. Pantoprazole is a substituted benzimidazole. Pantoprazole accumulates in the acidic compartment of the parietal cells after absorption and is protonated by specific action on the proton pumps of the parietal cells. Pantoprazole is a proton pump inhibitor, i.e., it inhibits specifically and dose proportionally H+,K+-ATPase, the enzyme which is responsible for gastric acid secretion in the parietal cells of the stomach.

Pantoprazole exerts its full effect in a strongly acidic environment (pH<3) and remains mostly inactive at higher pH values, thereby selectively affecting the acid secreting parietal cells of the stomach. Therefore, the complete pharmacological and therapeutic effect for pantoprazole can only be achieved in the acid-secreting parietal cells. By means of a feedback mechanism this effect is diminished at the same rate as acid secretion is inhibited.

As with other proton pump inhibitors and H2 receptor inhibitors, treatment with pantoprazole causes reduced acidity in the stomach causing a reversible increase in gastrin in proportion to the reduction in acidity. Since pantoprazole binds to the enzyme distal to the cell receptor level, it affects hydrochloric acid secretion independently of stimulation by other substances like acetylcholine, histamine, gastrin. The same effect is observed following oral or intravenous administration. In general, preparation of pantoprazole sodium sesquihydrate and certain of its polymorphic forms is known in the art. However, it is also known that different polymorphic forms of the same drug may have substantial differences in certain pharmaceutically important properties. Therefore, there is a continuing need for new methods of preparation.

SUMMARY OF THE INVENTION

In accordance with one aspect, the invention provides a process for making crystalline Form I of Pantoprazole sodium sesquihydrate, the process including providing a solution of crystalline Form I of Pantoprazole sodium sesquihydrate in an sodium hydroxide solution; adding an anti-solvent to the reaction solution until a precipitate is formed; and isolating the precipitate, which is the crystalline Form I of Pantoprazole sodium sesquihydrate. Various embodiments and variants are provided.

Figure 1:
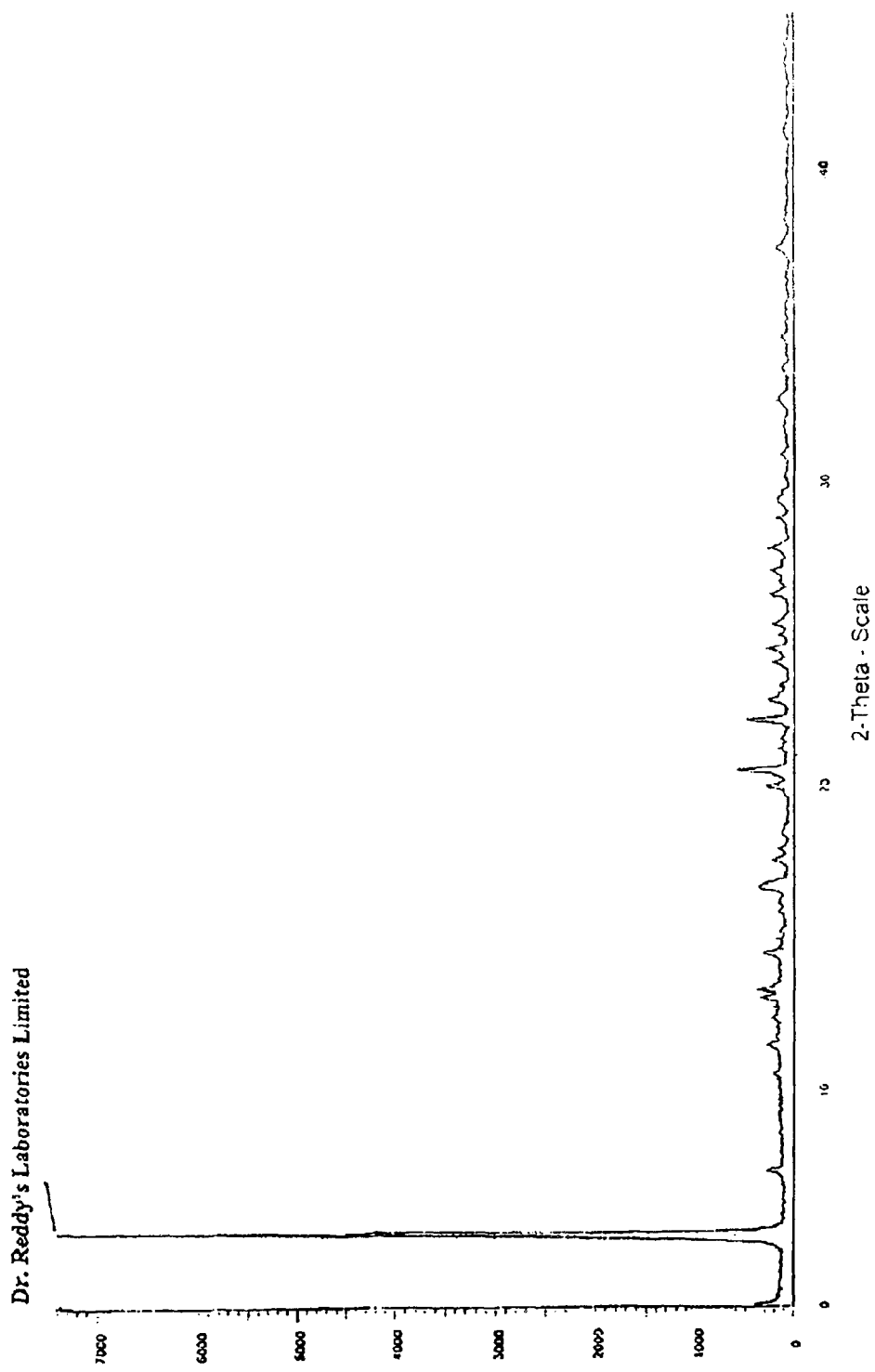
FIG. 1 shows a sample X-ray powder diffractogram of crystalline Form I of Pantoprazole sodium sesquihydrate prepared according to a prior art process.

DETAILED DESCRIPTION OF THE ACCOMPANYING DRAWINGS:

FIG. 1. is characteristic X-ray powder diffraction pattern of crystalline Form-I of Pantoprazole sodium sesquihydrate (according to process disclosed in J.Med.Chem., 1992, 35, 1049–1057).
Vertical axis: Intensity (CPS); Horizontal axis; Two Theta (degrees).

The significant two-theta values obtained are 5.238, 7.294, 10.523, 11.428, 12.345, 13.024, 13.30, 14.459, 15.207, 15.844, 16.15, 16.653, 17.527, 17.884, 18.404, 19.97, 20.486, 21.214, 22.148, 22.812, 23.26, 24.002, 24.497, 24.957, 25.32, 26.278, 27.037, 27.798, 28.737, 28.383, 30.18, 30.861, 32.652, 33.647, 34.671 and 37.572 degrees two-theta.

Figure 2:
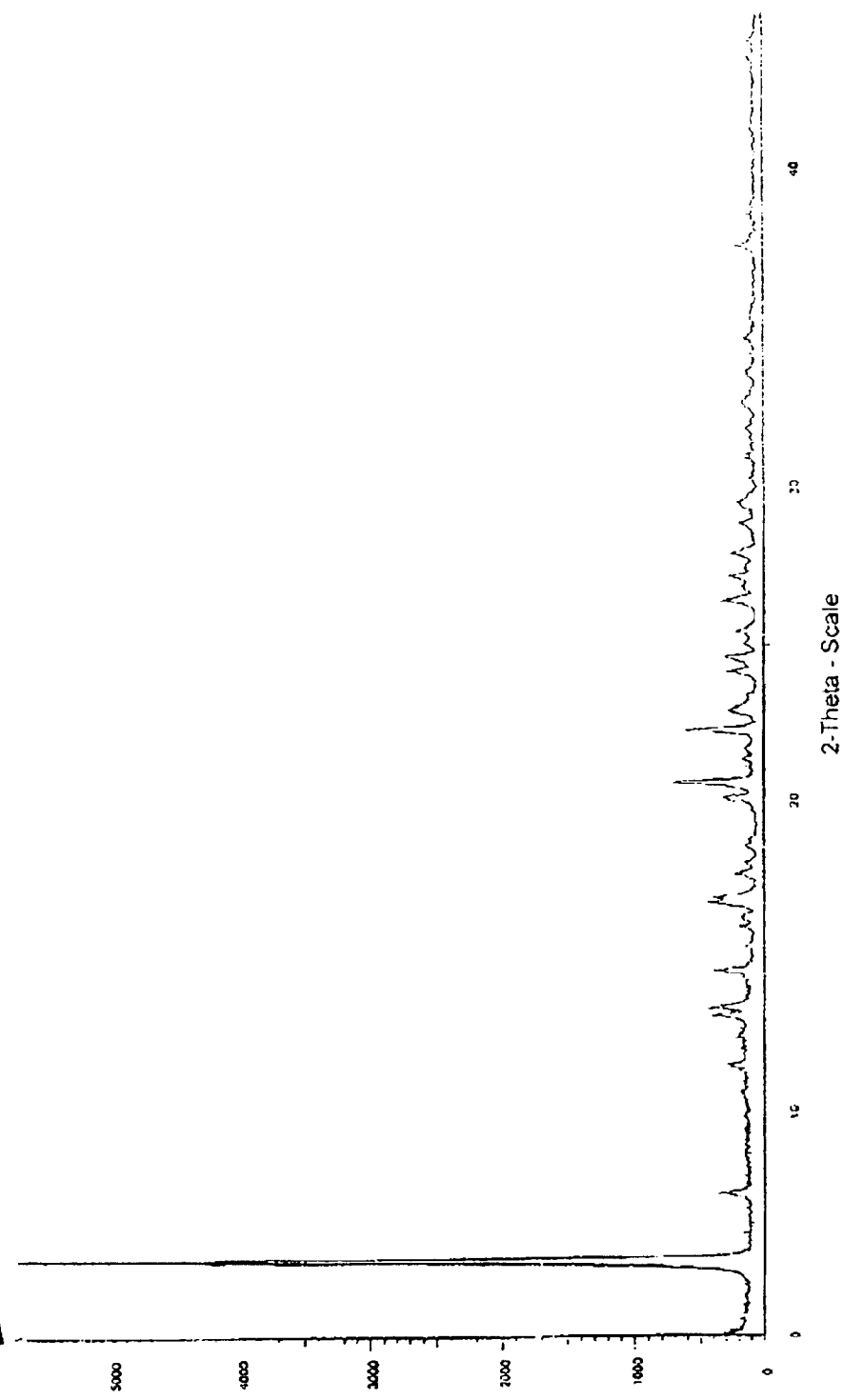
FIG. 2 is a sample X-ray power diffractogram of crystalline Form-I of Pantoprazole sodium sesquihydrate prepared by the inventors.

FIG. 2. is characteristic X-ray powder diffraction pattern of crystalline form-I of Pantoprazole sodium sesquihydrate.
Vertical axis: Intensity (CPS); Horizontal axis: 2 Theta (degrees).

The significant two-theta values obtained are 5.326, 7.385, 9.868,10.63, 11.531, 12.472, 13.102, 13.366, 14.543, 15.317, 15.92, 16.207, 16.687, 16.836, 17.62, 17.966, 18.498, 20.061, 20.581, 21.271, 21.621, 22.254, 22.886, 23.33, 24.122, 24.587, 25.026, 25.405, 26.353, 26.803, 27.147, 27.887, 28.842, 29.487, 30.926, 31.878, 32.708, 33.694, 34.748 and 37.642 degrees two-theta.

DESCRIPTION OF PREFERRED EMBODIMENTS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Unless stated to the contrary, any use of the words such as "including," "containing," "comprising," "having" and the like, means "including without limitation" and shall not be construed to limit any general statement that it follows to the specific or similar items or matters immediately following it. Except where the context indicates to the contrary, all exemplary values are intended to be fictitious, unrelated to actual entities and are used for purposes of illustration only. Most of the foregoing alternative embodiments are not mutually exclusive, but may be implemented in various combinations. As these and other variations and combinations of the features discussed above can be utilized without departing from the invention as defined by the claims, the foregoing description of the embodiments should be taken by way of illustration rather than by way of limitation of the invention as defined by the appended claims.

For purposes of the present invention, the following terms are defined below.

"Pharmaceutically acceptable" means that which is useful in preparing a pharmaceutical composition that is generally non-toxic and is not biologically undesirable and includes, but is not limited to, that which is customarily utilized for veterinary use and/or human pharmaceutical use.

"Anti-solvent" is a solvent which when added to an existing solution of a substance reduces the solubility of the substance.

The term "composition" includes, but is not limited to, a powder, a solution, a suspension, a gel, an ointment, an emulsion and/or mixtures thereof. The term composition is intended to encompass a product containing the specified ingredient(s) in the specified amount(s), as well as any product, which results, directly or indirectly, from combination of the specified ingredients in the specified amounts. A "composition" may contain a single compound or a mixture of compounds. A "compound" is a chemical substance that includes molecules of the same chemical structure.

The term "pharmaceutical composition" is intended to encompass a product comprising the active ingredient(s), pharmaceutically acceptable excipients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing the crystalline Form I of Pantoprazole sodium sesquihydrate, additional active ingredient(s), and pharmaceutically acceptable excipients.

The term "excipient" means a component of a pharmaceutical product that is not the active ingredient, such as filler, diluent, carrier, and so on. The excipients that are useful in preparing a pharmaceutical composition are preferably generally safe, non-toxic and neither biologically nor otherwise undesirable, and are acceptable for veterinary use as well as human pharmaceutical use. "A pharmaceutically acceptable excipient" as used in the specification and claims includes both one and more than one such excipient. "Therapeutically effective amount" means the amount of a compound that, when administered for treating or preventing a disease, is sufficient to effect such treatment or prevention for the disease. The "therapeutically effective amount" will vary depending on the compound, the disease and its severity and the age, weight, etc., of the patient to be treated.

When referring to a chemical reaction, the terms "treating", "contacting" and "reacting" are used interchangeably herein and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "substantially free of" in reference to a composition, as used herein, means that the substance from which the composition is free of cannot be detected by methods known to those skilled in the art.

Pantoprazole sodium sesquihydrate has the chemical structure

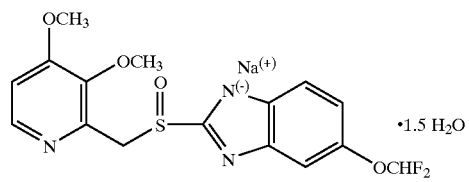

Pantoprazole is disclosed, for example, in U.S. Pat. No. 4,758,579, which is incorporated herein by reference in its entirety, and specifically for the purpose of showing how Pantoprazole is prepared and characterized. An article from the Journal of Medicinal Chemistry, 35:1049–1057 (1992), incorporated herein by reference, specifically for the purpose of showing how Pantoprazole sodium sesquihydrate is prepared, discloses the preparation of Pantoprazole sodium sesquihydrate.

Different solid forms of the same drug may exhibit different properties, including characteristics that have functional implications with respect to their use as active ingredients of pharmaceutical products. For example, polymorphs of the same drug may have substantial differences in such pharmaceutically important properties as dissolution rates and bioavailability. Likewise, different polymorphs may have different processing properties, such as hydroscopicity, flowability, and the like, which could affect their suitability as active pharmaceuticals for commercial production.

An improved process for the synthesis of 5-(Difluoromethoxy)-2-[[(3,4-dimethoxy-2-pyridinyl) methyl]sulfinyl]-1H-benzimidazole sodium sesquihydrate was found by the inventors. The object of the improved process was to provide a cost effective, substantially pure, easily scaleable, environmentally friendly process. The chemical route to prepare pantoprazole sodium sesquihydrate is known and described in an article from the Journal of Medicinal Chemistry, 35:1049–1057 (1992), which is hereby incorporated by reference in its entirety. The inventors found that the synthesis of pantoprazole sodium sesquihydrate can be achieved by dissolving pantoprazole free base in a sodium hydroxide solution, filtering the solution and adding an anti-solvent to isolate the crystalline compound. A smaller volume of solvents and reagents can be used in this process. For example C1–C4 straight or branched chain alcohols, tetrahydrofuran and ethyl acetate are suitable solvents. Suitable anti-solvents are petroleum ether, hexane, n-heptane, cyclohexane, cycloheptane or chlorinated solvents such as dichloromethane or chloroform or ethereal solvents, such as diisopropyl ether or methylteriary butyl ether.

Less solvent, both in terms of the number of solvents and the volume of solvent used, is used in this process, making this process both economical and environmentally friendly.

The preparation described in the prior art is not economical for large-scale synthesis due to the number of reagents and the volume of reagents used in the prior art process. The isolation of Pantoprazole sodium sesquihydrate is problematic because of the high volume of solvent used in the prior art process, particularly ethanol, which makes it difficult to isolate the Pantoprazole sodium sesquihydrate product. The yields and purity of the Pantoprazole sodium sesquihydrate is low. A reduction in the volume of ethanol is required to render the Pantoprazole sodium sesquihydrate produced by the prior art process pharmaceutically acceptable.

The crystalline Form-I of Pantoprazole sodium sesquihydrate of the present invention is characterized by X-ray Powder diffractogram, Differential Scanning Colorimetry thermogram and Infrared spectra.

The X-ray powder diffractogram of the crystalline Form-I of pantoprazole sodium sesquihydrate of the present invention and the prior art crystalline Form-I of Pantoprazole sodium sesquihydrate are measured on a Bruker Axs, D8 Advance Powder X-ray Diffractometer with Cu K alpha-1 Radiation source. The pattern of X-ray diffractogram of these two compounds is found to be identical.

The X-ray powder diffractogram of prior art crystalline Form-I of Pantoprazole sodium sesquihydrate is substantially as depicted in FIG. (1).

The X-ray powder diffractogram of the crystalline Form-I of pantoprazole sodium sesquihydrate obtained in the present inventive process is substantially as depicted in FIG. (2).

The characteristic peaks (in 2-theta values) and their relative intensities (in percentage) of crystalline Form-I of pantoprazole sodium sesquihydrate are shown in the following table (1).

TABLE 1

| Prior art crystalline Form-I of Pantoprazole sodium sesquihydrate | | Crystalline Form-I of Pantoprazole sodium sesquihydrate obtained in the present process | |
|---|---|---|---|
| 2θ(°) | Intensity (%) | 2θ(°) | Intensity (%) |
| 5.238 | 100 | 5.326 | 100 |
| 20.486 | 7.6 | 20.581 | 13.0 |
| 22.148 | 6.2 | 22.254 | 10.5 |
| 16.653 | 4.2 | 16.687 | 6.7 |
| 13.3 | 3.3 | 16.836 | 6.0 |
| 19.97 | 3.3 | 14.543 | 5.3 |
| 24.497 | 3.1 | 20.061 | 4.9 |
| 14.459 | 2.9 | 13.366 | 4.8 |
| 22.812 | 2.9 | 24.587 | 4.8 |
| 13.024 | 2.8 | 13.102 | 4.5 |
| 26.278 | 2.7 | 26.353 | 4.5 |
| 27.798 | 2.7 | 7.385 | 4.2 |
| 7.294 | 2.7 | 22.886 | 4.0 |
| 27.037 | 2.5 | 24.122 | 3.7 |
| 24.002 | 2.4 | 17.62 | 3.2 |
| 25.32 | 2.3 | 27.887 | 3.1 |
| 17.527 | 2.2 | 11.531 | 2.8 |
| 37.572 | 2.0 | 27.147 | 2.7 |
| 11.428 | 1.7 | 37.642 | 2.5 |
| 28.737 | 1.7 | 25.405 | 2.4 |
| 29.383 | 1.6 | 29.487 | 2.4 |
| 17.884 | 1.5 | 16.207 | 1.7 |
| 32.652 | 1.4 | 17.966 | 1.6 |
| 24.957 | 1.3 | 18.498 | 1.5 |
| 10.523 | 1.1 | 15.92 | 1.4 |
| 30.861 | 1.1 | 25.026 | 1.4 |
| 34.671 | 1.1 | 34.748 | 1.3 |
| 15.844 | 1 | 26.803 | 1.2 |
| 18.404 | 1 | 21.271 | 1.2 |
| 21.214 | 1 | 33.694 | 1.1 |
| 23.26 | 1 | 12.472 | 1 |
| 33.647 | 1 | 15.317 | 1 |
| 12.345 | 0.9 | 23.33 | 1 |
| 16.15 | 0.8 | 31.878 | 1 |
| 15.207 | 0.7 | 28.842 | 1.9 |
| 30.18 | 0.6 | 21.621 | 0.9 |
| — | — | 30.926 | 0.9 |
| — | — | 10.63 | 0.8 |
| — | — | 9.868 | 0.6 |

The crystalline Form-I of pantoprazole sodium sesquihydrate of the present invention is also characterized by Differential scanning calorimetry. The Differential scanning calorimetry thermogram exhibits a significant endo peak around 136° C.

The crystalline Form-I of pantoprazole sodium sesquihydrate of the present invention is further characterized by Infrared spectrum, which is measured by KBr-transmission method.

The identified significant IR bands are observed around 456, 477, 500.7, 532.3, 575.2, 397.3, 643.9, 685.6, 719.8, 764.4, 804.3, 860.4, 909.1, 922.8, 986.6, 1028.1, 1065.0, 1087.7, 1113.0, 1139.9, 1171.5, 1293.0, 1319.6, 1365.3, 1383.7, 1401.3, 1467.9, 1490.3, 1572.3, 2059.8, 2600.5, 2639.0, 2666.5, 2697.2, 2741.5, 2794.9, 2867.9, 3030.0, 3061.0, 3290.6.

In one embodiment of this aspect of the invention, the process for the preparation of 5-(Difluoromethoxy)-2-[[(3,4-dimethoxy-2-pyridinyl)methyl]sulfinyl]-1H-benzimidazole sodium sesquihydrate includes:

a) reacting pantoprazole free base with a stoichiometric amount of aqueous sodium hydroxide in a solvent comprising of C1–C4 straight or branched chain alcohols, tetrahydrofuran or ethyl acetate, at a temperature of 25–50° C.;

b) optionally filtering the reaction solution;

c) adding a solvent comprising of aliphatic or alicyclic hydrocarbon solvent, such as petroleum ether, hexane, n-heptane, cyclohexane, cycloheptane or chlorinated solvents such as dichloromethane or chloroform or ethereal solvents, such as diisopropyl ether or methyl-tertiary butyl ether at a temperature of −10 to +20° C.;

d) stirring the solution till the solid separates;

e) filtering the solid by conventional methods;

f) drying the resulted solid under vacuum at a temperature of 40–90° C., preferably 40–50° C. to a constant weight to afford crystalline Form-1 of Pantoprazole sodium sesquihydrate.

Suitable solvents for dissolving Pantoprazole freebase include C1–C4 straight or branched alcohols such as methanol, ethanol, n-propanol, isopropanol, n-butanol, secondary butanol or tertiary butanol or other solvents such as tetrahydrofuran or acetonitrile or ethylacetate containing stoichiometric amount of aqueous sodium hydroxide solution. The preferred solvent for dissolution is tetrahydrofuran, acetonitrile or ethyl acetate.

Suitable solvents for isolating the desired crystalline Form-I of Pantoprazole sodium sesquihydrate as an anti solvent include aliphatic or alicyclic hydrocarbon solvents comprising of petroleum ether, hexane, n-heptane, cyclohexane or cyclo heptane, or chlorinated solvents such as dichloromethane or chloroform or ethers having C1–C4 carbon atoms in straight or branched chain such as dimethyl ether, diethyl ether, di isopropyl ether, di butyl ether or methyl tertiary butyl ether. The preferred anti solvents are dichloromethane or diisopropylether or methyl-tertiary butyl ether.

The inventors of the present invention prepared the desired crystalline Form-I of Pantoprazole sodium sesquihydrate from various solvents and analyzed the crystalline structure by X-ray diffractogram, which are substantially identical. The laboratory findings are tabulated in the following table (2).

TABLE 2

| Pantoprazole free base (in grams) | Dissolution solvent/volume (in ml) | Anti Solvent/ Volume (in ml) | Yield (in grams) | Moisture content (%) | XRD |
|---|---|---|---|---|---|
| 75 | Tetrahydrofuran/525 | Methyl tertiary butyl ether/675 | 74.6 | 6.43 | Form-I |
| 25 | Tetrahydrofuran/200 | Isopropyl ether/225 | 22.2 | 6.45 | Form-I |

TABLE 2-continued

| Pantoprazole free base (in grams) | Dissolution solvent/volume (in ml) | Anti Solvent/ Volume (in ml) | Yield (in grams) | Moisture content (%) | XRD |
|---|---|---|---|---|---|
| 25 | Isopropylalcohol/200 | Isopropyl ether/225 | 23.4 | 6.86 | Form-I |
| 25 | Acetonitrile/200 | Methyl tertiary butyl ether/225 | 24.5 | 6.38 | Form-I |
| 25 | Acetonitrile/200 | Dichloromethane/225 | 21.4 | 6.88 | Form-I |
| 25 | Methanol/25 | Methyl tertiary butyl ether/550 | 16.4 | 6.4 | Form-I |
| 25 | n-Propanol/25 | Methyl tertiary butyl ether/300 | 16.8 | 6.30 | Form-I |
| 10 | 2-Butanol/20 | Methyl tertiary butyl ether/200 | 7.2 | 6.76 | Form-I |

The crystalline Form-I of pantoprazole sodium sesquihydrate obtained as per the above processes is observed as free flowing, non-solvated crystalline solid which is well suited for pharmaceutical applications. The process of the present invention is simple, non-hazardous and well suited for commercial production.

Also provided are pharmaceutical compositions containing a crystalline Form-1 of Pantoprazole sodium sesquihydrate and a pharmaceutically-acceptable carrier. In addition to the active compound, the pharmaceutical composition includes one or more pharmaceutically acceptable carriers, also known as excipients, which ordinarily lack pharmaceutical activity, but have various useful properties which may, for example, enhance the stability, sterility, bioavailability, and ease of formulation of a pharmaceutical composition. These carriers are pharmaceutically acceptable, meaning that they are not harmful to humans or animals when taken appropriately and are compatible with the other ingredients in a given formulation. The carriers may be solid, semi-solid, or liquid, and may be formulated with the compound in bulk, but ultimately in the form of a unit-dose formulation (i.e., a physically discrete unit containing a specific amount of active ingredient) such as a tablet or capsule. The pharmaceutical compositions may include, in addition to a compound of this invention, one or more active pharmaceutical compounds.

Generally, the pharmaceutical compositions are prepared by uniformly admixing the active ingredient with liquid or solid carriers and then shaping the product into the desired form. The pharmaceutical compositions may be in the form of suspensions, solutions, elixirs, aerosols, or solid dosage forms. Because of their ease of administration, tablets and capsules represent the most advantageous oral dosage unit form, in which case solid pharmaceutical carriers are employed.

The more preferred oral solid preparation is a tablet. A tablet may be prepared by direct compression, wet granulation, or molding, of the active ingredient(s) with a carrier and other excipients in a manner known to those skilled in the art. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made on a suitable machine, a mixture of the powdered compound moistened with an inert liquid diluent. are suitable in the case of oral solid dosage forms (e.g., powders, capsules, and tablets). If desired, tablets may be coated by standard techniques. The compounds of this invention may be formulated into typical disintegrating tablet, or into a controlled or extended release dosage forms. Examples of suitable controlled release formulation vehicles are disclosed in U.S. Pat. Nos. 3,845,770; 3,916,899; 3,536,809; 3,598,123; and 4,008,719, incorporated herein by reference in their entireties.

The pharmaceutical compositions are contemplated in various formulations suitable for various modes of administration, including but not limited to inhalation, oral, rectal, parenteral (including subcutaneous, intradermal, intramuscular, intravenous), implantable, intravaginal and transdermal administration. The most suitable route of administration in any given case depends on the duration of the subject's condition, the length of treatment desired, the nature and severity of the condition being treated, and the particular formulation that is being used. The formulations may be in bulk or in unit dosage form, and may be prepared by methods well known in the art for a given formulation.

The amount of active ingredient included in a unit dosage form depends on the type of formulation in which the active ingredient is presented. A pharmaceutical composition will generally contain about 0.1% by weight to about 99% by weight of active ingredient, preferably about 1% by weight to 50% by weight for oral administration and about 0.2% by weight to about 20% by weight for parenteral administration.

Formulations suitable for oral administration include capsules (hard and soft), cachets, lozenges, syrups, suppositories, and tablets, each containing a pre-determined amount of the active compound; as a powder or granules; as a solution or a suspension in an aqueous or non-aqueous liquid; or as an oil-in-water or water-in-oil emulsion. Such formulations may be prepared by any suitable method of pharmacy that includes the step of bringing into association the active compound and a suitable carrier or carriers. Preferred oral or internal dosage forms may include, for example, between 1 mg and 40 mg of Pantoprazole sodium sesquihydrate. The amount of active ingredient per unit dosage of solid formulations is preferably from about 20 mg to about 40 mg, preferably about 40 mg. For liquid oral formulations, a preferable amount is from about 2% by weight to about 20% by weight. Suitable carriers include but are not limited to fillers, binders, lubricants, inert diluents, surface active/dispersing agents, flavorants, antioxidants, bulking and granulating agents, adsorbants, preservatives, emulsifiers, suspending and wetting agents, glidants, disintegrants, buffers and pH-adjusting agents, and colorants. Examples of carriers include celluloses, modified celluloses, cyclodextrins, starches, oils, polyols, sugar alcohols and sugars, and others. For liquid formulations sugar, sugar alcohols, ethanol, water, glycerol, and poyalkylene glycols are particularly suitable, and may also be used in solid formulations. Cyclodextrins may be particularly useful for increasing bioavailability. Formulations for oral administration may optionally include enteric coatings known in the art to prevent degradation of the formulation in the stomach and provide release of the drug in the small intestine. Example of suitable pantoprazole dosage form is disclosed in U.S. Pat. No. 6,559,188, which is incorporated herein by reference in its entirety and for purposes of showing doses of pantoprazole and formulation methodologies.

Formulations suitable for buccal or sub-lingual administration include lozenges comprising the active compound in a flavored base, usually sucrose and acacia or tragacanth, although other agents are also suitable, and pastilles comprising the compound in an inert base such as gelatin and glycerin or sucrose and acacia.

Formulations suitable for parenteral administration comprise sterile aqueous and non-aqueous injection solutions of the active compound, preferably isotonic with the blood of the intended recipient. The amount of active ingredient is preferably now about 0.1% by to about 80% by weight.

These preparations may contain, among other ingredients, anti-oxidants, buffers, bacteriostats, and solutes that render the formulation isotonic with the blood of the intended recipient. Aqueous and non-aqueous sterile suspensions may include, among others, suspending and thickening agents. The formulations may be presented in unit-dose or multi-dose containers, e.g., sealed capsules and vials, and may be stored in a freeze-dried or lyophilized condition requiring only the addition of the sterile liquid carrier, for example, saline or water-for-injection immediately prior to use. Extemporaneous injection solutions and suspensions may be prepared from sterile powders, granules and tablets of the kind previously described.

Formulations suitable for rectal administration are preferably presented as unit dose suppositories. These may be prepared by admixing the active compound with one or more conventional solid carriers, e.g., cocoa butter, and then shaping the resulting mixture.

Formulations suitable for transdermal delivery include ointments, creams, lotions, and oils and contain well-known pharmaceutically and cosmetically suitable ingredients. Bases for such formulations include for example alcohols, lanolin, petrolatum, paraffin, polyethylene glycol, emulsifiers, penetration enhancing agents, and oleaginous vehicles such as oils. Skin patches may also be used, typically consisting of a fabric or paper base impregnated with a suitable dose in a transdermal formulation. Formulations suitable for transdermal administration may also be delivered by iontophoresis, and typically take the form of an optionally buffered aqueous solution of the active compound.

The compounds of this invention may be combined with or linked to other compounds to obtain desired properties, for example the compounds of this invention may be linked to a stabilizing polymer such as a polyalkylene glycol (such as polyethylene glycol), or linked to a targeting compound such as an antibody. The resulting linked compounds are also part of this invention.

In another aspect, the invention also provides methods of treatment using the compounds and the pharmaceutical compositions of this invention. The compounds and compositions of this invention may be administered to a subject in an amount effective to stimulate insulin release by said subject. Further, the compounds and compositions of this invention may be administered to a subject for treating a disorder related to insulin release by administering to a subject an amount effective to stimulate insulin release by said subject. Methods for treating diabetes in a subject by administering a compound or composition of this invention to a subject in an amount effective to eliminate or alleviate symptoms of diabetes, or to prevent excessive blood sugar levels or reduce blood sugar levels, are also part of this invention. Methods for regulating blood sugar levels in a subject by administering an amount of a compound or composition of this invention effective to regulate blood sugar levels in the subject are also part of this invention.

In general, the treatment may be determined to alleviate, to eliminate, or to prevent a given condition based on factors determinable by a skilled physician as discussed below in the context of determining an effective amount for dosage.

By subject is meant a human or an animal, preferably human. Animals contemplated by this invention include any animal safely treatable by compounds of this invention, preferably mammals such as bovines, ovines, caprines, equines, felines, canines, rodents, leporids, and other mammalian farm and zoo animals or domestic pets.

The effective amount (i.e., dosage) of active compound for treatment will vary depending on the route of administration, the condition being treated, its severity, and duration, and the state and age of the subject. A skilled physician will monitor the progress of the subject and will adjust the dosage accordingly, depending on whether the goal is to eliminate, alleviate, or prevent a given condition. Generally, the dosage should be considered in proportion to the subject's weight. Depending on the solubility of the particular formulation of active compound administered, the daily dose may be divided among one or several unit dose administrations. For example therapeutic administration about fifteen to thirty minutes before main meals is preferable (i.e. three times daily), although administration of the active compounds may be carried out prophylactically, and may be maintained for prolonged periods of time. One skilled in the art will take such factors into account when determining dosage. In general dosages will be in the range of about 20–40 mg daily.

The examples that follow are not intended to limit the scope of the invention as defined hereinabove or as claimed below.

EXAMPLE-1

Pantoprazole free base (50 grams) was dissolved in a solution of tetrahydrofuran (350 ml) and aqueous sodium hydroxide solution (5.4 grams dissolved in 10 ml of water), and stirred at a temperature of 25–35° C. till the clear solution results. The reaction solution was filtered through hyflow and washed the bed with tetrahydrofuran (2×25 ml). Dichloromethane (400 ml) was added slowly to the filtrate over a period of about 1 hour and stirred for about 5–6 hours to crystallize the solid mass. The separated solid mass was cooled to a temperature of 5–10° C. and further stirred for about 2–3 hours. The solid was filtered, washed with dichloromethane (2×25 ml) and suck dried under vacuum. The wet solid was suspended in dichloromethane (250 ml) and stirred for about 15–30 minutes. Then the solid was filtered and suck dried under vacuum and further dried at a temperature of 40–50° C. to afford crystalline Form-I of Pantoprazole sodium sesquihydrate.

(Weight: 50.4 grams, MC: 6.49% w/w)

EXAMPLE-2

Pantoprazole free base (25 grams) was dissolved in a solution of acetonitrile (175 ml) and aqueous sodium hydroxide solution (2.7 grams in 5 ml of water) and stirred at a temperature of 25–35° C. till the clear solution results. The reaction solution was filtered through hyflow and washed the bed with acetonitrile (25 ml). Isopropyl ether (225 ml) was added slowly to the filtrate over a period of about ½ hour and the filtrate was stirred for about 1–2 hours to crystallize the solid mass. The separated solid mass was cooled to a temperature of 5–10° C. and further stirred for 3–4 hours. The solid was filtered, washed with Isopropyl ether (25 ml) and suck dried under vacuum. The wet solid was further dried at a temperature of 40–50° C. to afford crystalline Form-I of Pantoprazole sodium sesquihydrate.

(Weight: 25.4 grams, MC: 6.55% w/w)

EXAMPLE-3

Pantoprazole freebase (25 grams) was dissolved in a solution of ethyl acetate (50 ml) and aqueous sodium hydroxide solution (2.7 grams in 5 ml of water) and stirred at a temperature of 40–50° C. till the clear solution results. Methyl tertiary butyl ether (250 ml) was added to the reaction mixture and stirred for about 3–4 hours to crystallize the solid mass. The separated solid mass was filtered, washed with methyl tertiary butyl ether (50 ml) and suck dried under vacuum. The wet solid was further dried at a temperature of 40–50° C. to afford crystalline Form-I of Pantoprazole sodium sesquihydrate.

(Weight: 15.6 grams, MC: 7.07% w/w)

Unless stated to the contrary, words and phrases such as "including," "containing," "comprising," "having," "for example", "i.e.", "in particular" and the like, means "including without limitation" and shall not be construed to limit any general statement that it follows to the specific or similar items or matters immediately following it. Except where the context indicates to the contrary, all exemplary values are intended to be used for purposes of illustration. Most of the foregoing alternative embodiments are not mutually exclusive, but may be implemented in various combinations. As these and other variations and combinations of the features discussed above can be utilized without departing from the invention as defined by the claims, the foregoing description of the embodiments should be taken by way of illustration rather than by way of limitation of the invention as defined by the appended claims.

We claim:

1. A process for preparing crystalline Form-I of Pantoprazole sodium sesquihydrate, comprising:

dissolving Pantoprazole free base in a solvent containing a stoichiometric amount of aqueous sodium hydroxide;

b) adding an anti-solvent;

c) cooling the mixture of (a) and (b) until a precipitate is formed; and d) isolating crystalline Form-I of Pantoprazole sodium sesquihydrate.

2. The process of claim 1, further comprising drying the isolated Pantoprazole sodium sesquihydrate.

3. The process of claim 1, wherein said solvent is a $C_1$–$C_4$ straight or branched alcohol, tetrahydrofuran, acetonitrile, or ethyl acetate.

4. The process of claim 1, wherein said solvent is tetrahydrofuran, acetonitrile or ethyl acetate.

5. The process of claim 1, wherein said anti-solvent is an aliphatic or alicyclic hydrocarbon solvent a chlorinated solvent, or an ether of groups having 1–4 carbon atoms in a straight or branched chain.

6. The process of claim 1, wherein said anti-solvent is dichloromethane or diisopropylether or methyl-tertiary butyl ether.

7. The process of claim 1, wherein said dissolving step comprises heating a mixture of the starting Pantoprazole free base and the solvent to a temperature of from about 25° C. to about 50° C. until the solution is formed.

8. The process of claim 7, wherein the mixture is heated to from about 40° C. to about 50° C.

9. The process of claim 1, further comprising filtering said provided solution of Pantoprazole prior to said cooling step.

10. The process of claim 1, wherein the solution of Pantoprazole is cooled to from about −10° C. to about 20° C.

* * * * *